United States Patent [19]
MacGregor

[11] Patent Number: 5,015,253
[45] Date of Patent: May 14, 1991

[54] NON-WOVEN ENDOPROSTHESIS

[75] Inventor: David C. MacGregor, Miami, Fla.

[73] Assignee: Cordis Corporation, Miami, Fla.

[21] Appl. No.: 366,676

[22] Filed: Jun. 15, 1989

[51] Int. Cl.$^5$ .............................................. A61F 2/06
[52] U.S. Cl. .......................................... 623/1; 623/13
[58] Field of Search ...................... 623/1, 13; 267/166, 267/167; 128/343, 345; 606/191, 194, 195

[56] References Cited

U.S. PATENT DOCUMENTS

| | | |
|---|---|---|
| 3,490,975 | 1/1970 | Lightwood et al. . |
| 3,526,005 | 9/1970 | Bokros et al. .......................... 623/1 |
| 3,842,441 | 10/1974 | Kaiser .................................. 623/13 |
| 3,868,956 | 3/1975 | Alfidi et al. . |
| 4,469,101 | 9/1984 | Coleman et al. ...................... 623/13 |
| 4,475,972 | 10/1984 | Wong et al. . |
| 4,503,569 | 3/1985 | Dotter . |
| 4,512,338 | 4/1985 | Balko et al. . |
| 4,553,545 | 11/1985 | Maass et al. . |
| 4,619,246 | 10/1986 | Molgaard-Nielsen et al. ..... 128/345 |
| 4,649,922 | 3/1987 | Wiktor . |
| 4,655,771 | 4/1987 | Wallsten . |
| 4,739,762 | 4/1988 | Palmaz . |
| 4,800,882 | 1/1989 | Gianturco ............................ 623/13 |
| 4,830,003 | 5/1989 | Wolf et al. ............................ 623/1 |
| 4,856,516 | 8/1989 | Hillstead ............................... 623/1 |

FOREIGN PATENT DOCUMENTS 0282175 9/1988 European Pat. Off. .
1205743 9/1970 United Kingdom .

OTHER PUBLICATIONS

Annis et al., An Elastomeric Vascular Prosthesis, 24, [Trans. Am. Soc. Artif. Intern. Organs, 209 (1978).
Leidner et al., A Novel Process for the Manufacturing of Porous Grafts: Process Description and Product Evaluation, 17, J. Biomed. Mat. Res., 229 (1983).
Wilson et al., Anisotropic Polyurethane Nonwoven, Conduits: A New Approach to the Design of a Vascular Prosthesis, 29, Trans. Am. Soc. Artif. Intern. Organs, 260 (1983).

Primary Examiner—David J. Isabella
Attorney, Agent, or Firm—Lockwood, Alex, FitzGibbon & Cummings

[57] ABSTRACT

A generally tubular endoprosthesis or stent that includes a non-woven structure formed by two or more generally helically shaped cylinders of stiff strand material is provided. The strand material forming the non-woven structure is preferably secured together at attachment sites thereby allowing the stent to be flexible and adjustable to meet various application needs. Typically, these attachment sites will be somewhat frangible. The method used to make the endoprosthesis allows the architecture of the non-woven structure of the endoprosthesis to be varied according to the application for which the device is intended.

12 Claims, 1 Drawing Sheet

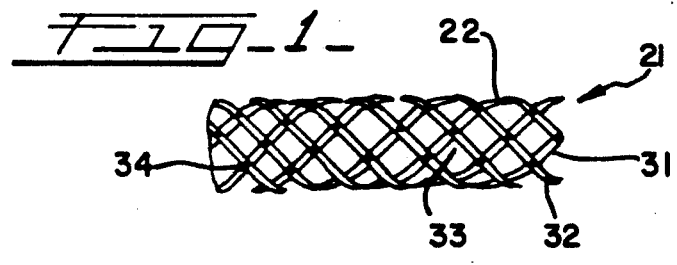
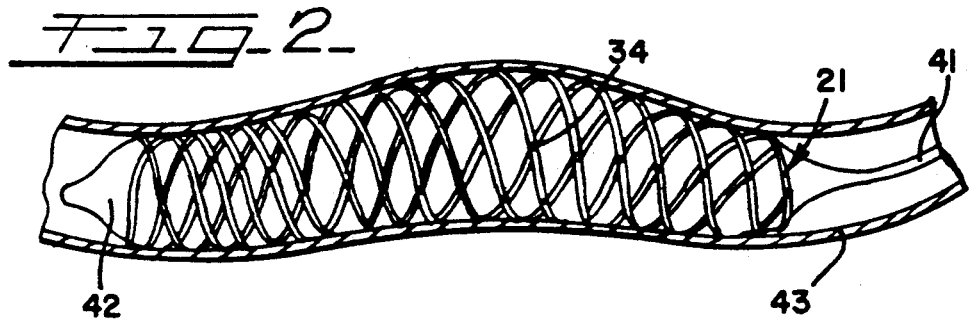
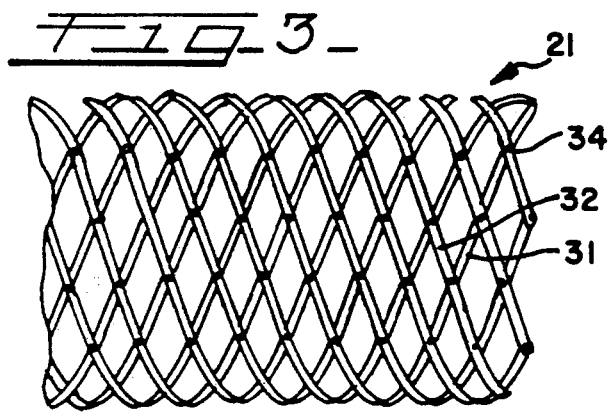
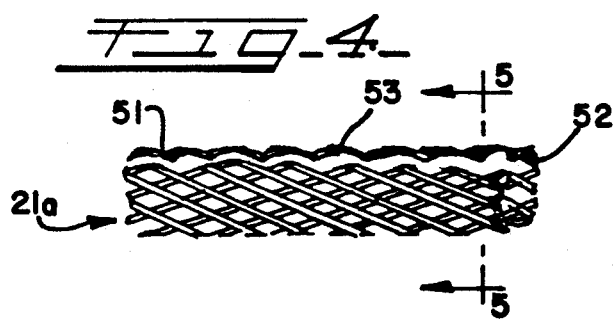
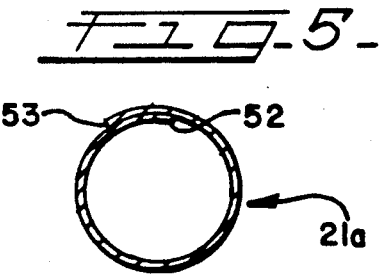
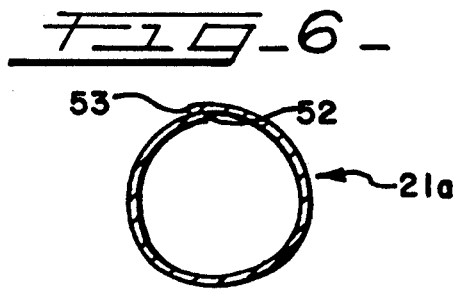

NON-WOVEN ENDOPROSTHESIS

BACKGROUND AND DESCRIPTION OF THE INVENTION

The present invention generally relates to endoprosthesis devices and to a method for making same, More particularly, the invention relates to a generally tubular endoprosthesis that includes a non-woven structure. The non-woven structure may include one or more layers of stiff strand material wound in a generally helical shape. The strand forming one layer may be bonded to the strand forming another layer at their mutual points of contact thereby facilitating the circumferential adjustability and flexibility of the device. Fixing the non-woven structure at the bonding points further allows the structure to be cut to various lengths and angles without the risk of fraying or unraveling. The non-woven structure allows the endoprosthesis to be deformed as desired in a permanent, non-uniform manner for irregularly shaped vascular system applications. The method used to make the present invention allows the architecture of the non-woven structure to be varied according to the application to which the device is put.

Blood vessels or other hollow organs may suffer from a variety of failings and disabilities such as abnormal widening (aneurysm), abnormal localized contraction or lesion growth (stenosis or occlusion), or abnormal narrowing (stricture). One surgical and medical technique employed to correct defective blood vessels or other hollow organs utilizes the insertion of a vascular endoprosthesis, commonly referred to as a "stent", in the blood vessel or other hollow organs. An endoprosthesis device of this type is typically placed or implanted by a mechanical transluminal procedure. Where the blood vessel or other hollow organs are abnormally widened, the stent is inserted to provide inner support to the blood vessel wall and to prevent further dilation and possible actual rupture. Where the endoprosthesis is used to treat a stenotic condition, the vessel must first be widened or dilated. Typically, this is done in association with a dilation element such as an angioplasty balloon. The dilation element is used to open the narrowing. Because stenotic lesions typically have a high fibrocollagenous content, the opened blood vessel or other hollow organs may begin to close upon removal of the dilation element. To prevent, or, at least, slow the post-dilation narrowing of the inner blood vessel wall tissue (that is, restenosis), a stent may be inserted contemporaneously. The insertion of the stent avoids the use of traditional surgical solutions to vascular problems. These traditional solutions carry with them inherent complications such as vessel wall dissection, subintimal flap formation, rupture, pseudoaneurysm formation, spasm, and late vessel narrowing (stenosis).

To accomplish the application objectives, a stent must be flexible, yet mechanically durable. A stent must be flexible so that it can be maneuvered within the blood vessel or other hollow organs without causing damage to the vessel. A stent must be flexible also so that it may be bent to the shape of the vessel in which it is positioned. Flexibility is necessary further because the stent may be located in an area which undergoes considerable movement or flexing.

The durability requirement for a stent arises largely from the methods conventionally utilized to deploy stents. For example, in one deployment method, a stent is compressed circumferentially so that it be may fitted within a tubular body, such as a catheter. The tubular body and stent are inserted percutaneously and moved to the desired vascular location, where the stent is released. The stent may also be deployed by compressing it to a diameter small enough to fit snugly around a collapsed angioplasty balloon. This assembly is then introduced into the blood vessel and moved to the affected area, at which location the balloon is expanded. The stenotic lesion is dilated and, upon the deflation of the balloon, the now expanded stent remains to prevent restenosis. In this deployment method, the stent must be sufficiently flexible in order to expand along with the balloon, yet be mechanically durable so the stent does not collapse during expansion. The stent must be also mechanically durable so the stent structure can support the dilated tissue during its possible recoil and withstand the movement or flexing which takes places in certain vascular locations. A stent which cannot withstand mechanical stress will fracture thereby causing the traumatization of the surrounding blood vessel.

Conventionally, stents may be made from various materials. If the stent is formed from wire-like elements, the wire is generally made from metal or a metal alloy. One type of stent, such as the type taught in Alfidi et al. U.S. Pat. No. 3,868,956, utilizes a specific type of metal alloy with "memory function", that is, the ability to recover its initial configuration upon heating. By using such an alloy, a stent, in a non-compressed state, may be inserted into a blood vessel, heated, and thereby expanded to the original desired shape.

A variety of stent structures are conventionally known. For example, one type of expandable graft is made from woven stainless steel wire whose cross points are soldered with silver. A woven prosthesis similar to this type is taught in Wallsten U.S. Pat. No. 4,655,771. Another type of stent utilizes a spring-like wire structure. By tightly coiling the spring, a stent with a relatively small profile is produced which may be inserted through a blood vessel. By releasing the spring, the stent uncoils at the place of implantation. Illustrative of this type of coiled spring stent or endoprosthesis is Mass, et al. U.S. Pat. No. 4,553,545. A similar use of a compressed spring-like expandable element is taught in Wiktor U.S. Pat. No. 4,649,922. A multi-helix or braided stent which is also expandable is taught in Palmaz U.S. Pat. No. 4,733,665. Additionally, a closed pattern characterizes the structure of the percutaneous endovascular stent formed of stainless steel wire taught in Gianturco U.S. Pat. No. 4,580,568.

The present invention advantageously retains most of the desirable features of the various conventional stents or endoprosthesis, while avoiding many of their various deficiencies. In summary, the generally tubular endoprosthesis of this invention includes a generally slender, tubular body member formed from one or more layers of strand material. The strand material from which the body member is formed is not interwoven but is fabricated in a manner similar to that detailed in U.S. Pat. No. 4,475,972 to Wong, which is incorporated by reference hereinto. In the present invention, the strand material providing the non-woven structure is made preferably from any suitable non-elastomeric material. The strand may be drawn onto a mandrel to form two or more components which are continuously helical in shape. In an embodiment of the present invention, the strand may be drawn onto the mandrel to form layers. The strand orientation of adjacent layers may be the same or different and are typically generally opposite to each other. Each successive layer may be bonded together at the points at which the strand material overlaps in order to provide a mechanically durable, yet highly flexible structure whose architecture may be adjusted according to the needs of each particular application. Regardless whether the stent is single-layered or multi-layered, each layer may be approximately equal in thickness to the diameter of the strand material.

It is a general object of the present invention to provide an improved generally tubular endoprosthesis.

Another object of the present invention is to provide an improved endoprosthesis or stent having a tubular body formed from at least one or more non-woven layers.

Another object of the present invention is to provide an improved endoprosthesis or stent whose non-woven structure allows the device to be permanently shaped to conform to the irregularities of the vascular system.

Another object of the present invention is to provide an improved endoprosthesis or stent having a non-woven structure which permits the device to be cut into various lengths and angles without collapsing, fraying or unraveling.

Another object of the present invention is to provide an improved endoprosthesis or stent having a non-woven structure which is bound so that the endoprosthesis or stent may be flexible and accept compression or expansion and retain full structural integrity.

Another object of the present invention is to provide an improved endoprosthesis or stent which is of a uniform and low profile structure that insures consistently predictable performance and use within areas of limited dimensions.

Another object of the present invention is to provide an improved endoprosthesis or stent which is readily expandable by an expanding member such as the balloon of a catheter device.

These and other objects, features, and advantages of this invention will be clearly understood through consideration of the following detailed description.

BRIEF DESCRIPTION OF THE DRAWINGS

In the course of this description, reference will be made to the attached drawings, wherein:

FIG. 1 is an elevational side view illustrating an embodiment of a non-woven tubular endoprosthesis according to the present invention in a relatively unexpanded state suitable for transluminal movement;

FIG. 2 shows the non-woven tubular endoprosthesis according to the present invention as fitted over and differentially expanded from within by a balloon;

FIG. 3 is an elevational side view of a non-woven tubular endoprosthesis according to the present invention in a relatively expanded, or implanted state;

FIG. 4 is an elevational perspective view of one embodiment of a non-woven tubular endoprosthesis according to the present invention in which a slit is cut longitudinally into and through the body of the device;

FIG. 5 is an end view of one embodiment of the non-woven tubular endoprosthesis illustrated in FIG. 4 and compressed so that the free longitudinal edge portions considerably overlap; and FIG. 6 is an end view of the endoprosthesis illustrated in FIG. 4 and expanded so that the free longitudinal edge portions overlap to a lesser degree.

DESCRIPTION OF THE PARTICULAR EMBODIMENTS

FIG. 1 illustrates an especially advantageous embodiment of the present invention in which a radially expandable endoprosthesis or stent is generally designated as 21. Stent 21 includes a network of strand material 22. Strand 22 may be made from an suitable biocompatible non-elastomeric material, such as metal wire, stiff polymeric strands, carbon, ceramic materials, biodegradable materials, or combinations thereof. Metals include tantalum, titanium, stainless steel, and alloys such as those including tantalum, titanium and the like. Of the metals that may be used, titanium or tantalum are preferred because of their radiopacity and overall flexibility which is characteristic of the low modulus of elasticity of these types of materials. Preferred polymeric materials include polyesters (such as Dacron) and polyglycolic and polylactic acid (Vicryl).

The stent 21, whose structure may be adjusted to meet the application needs, may be fabricated according to a method similar to those methods disclosed in and on devices (not shown herein) such as those described in U.S. Pat. No. 4,475,972 to Wong. Strand 22 may be drawn from a bobbin traversing a path generally longitudinal of the mandrel onto which a non-molten strand is wound. Alternatively, the strand 22, when in a molten or semi-molten state, may be drawn from a spinneret-like apparatus. The mandrel may rotate or, alternatively, remain stationary. Because the size of the exterior diameter of the mandrel will determine the size of the uncompressed or unexpanded inner diameter of the stent 21, a stent 21 having any appropriate initial internal diameter size may be made by choosing a mandrel of the appropriate size.

An initial winding of the stent 21 is formed during a single pass operation, such as by allowing the bobbin or spinneret-like apparatus to move from one end of the mandrel to its other end. A component which is formed during such a single pass operation and then removed from the mandrel after this initial layer is formed, will have a continuous generally helical shape.

By allowing the bobbin or the spinneret-like apparatus to reciprocate, another winding is added to this initial winding. When the windings are wound at the same pitch angle, they will not intersect. When the windings have a sufficiently different pitch angle, they intersect so as to form an underlying layer 31 and an overlying layer 32. The strand 22 of the overlying layer 32 preferably is aligned in a direction different from and generally opposite to the direction of the strand material 22 forming the underlying layer 31. In this manner, a non-woven strand network, which may be double-helical in shape, may be made by allowing the bobbin or spinneret-like apparatus to reciprocate across the mandrel. The angle at which the strand material is drawn and wound onto the mandrel may be defined as an acute angle with respect to the axis of the graft or mandrel on which the strand material is wound. By varying the angle at which the strand material is wound onto the mandrel, the size and shape of the pores 33 formed by and within the network of overlapping layers of wire, and therefore the overall porosity of the stent 21, may be selected. Specifically, a smaller angle of winding generally will result in smaller-sized pores 33 and reduced total porosity of the stent.

The exterior diameter of the stent 21 is a function of the size of the strand 22 used to make the stent 21 and the number of strand layers. The appropriate exterior diameter depends on the requirements of the implantation application for which the stent 21 is designed. However, the exterior diameter of the stent 21 will be primarily limited by the smallest diameter of any blood vessel or other hollow organ to be encountered by the stent 21 during implantation.

The present invention may include bonding points 34 where one portion of the strand engages another portion thereof and at which the strand material is bonded to itself. Typically these bonding points will affix the underlying layer 31 to the overlying layer 32. Preferably the bonding points 34 may be to a certain degree frangible upon a change in the radius of the stent 21, such as when the stent 21 is compressed or expanded. The circumstances under which the stent 21 undergoes these changes are discussed below.

Bonding may be accomplished in a variety of ways. Thermal bonding may be achieved by drawing and laying down the strand in a heated or molten state onto the mandrel. Thermal bonding may be accomplished also by laying down the strand in a non-heated or a non-molten state onto the mandrel and heating the environment surrounding the strand to a temperature which is at, or near the melting point of the material from which the strand is formed. Thermal bonding to form the bonding points 34 also may be accomplished, where the strand material is a metal, by sintering the stent 21, with or without the application of external pressure, following the winding of the metallic strand material onto the mandrel. Thermal bonding of the bonding points 34 is preferable in comparison, for example, to the use of conventional soldering in that the former does not increase the thickness of the device at the bonding points as soldering does. Adhesives, which may be biocompatible and hemocompatible, may also be used for bonding purposes.

To prevent the collapsing, fraying or unraveling of the layers 31, 32 when they are cut to various lengths and angles in forming a stent having a desired length and/or shape, the strand material from which the stent 21 is thus formed may be cropped closely to the bonding points 34 or may be curled under.

Because of the open architecture of the external surface of the stent 21, the endothelial tissue of the blood vessel or other hollow organ is not destroyed during a dilation procedure. Furthermore, the patches of endothelium which may be present in the pores of the stent 21 will facilitate the quick integration of the stent 21 into the wall of blood vessel or the like.

While the use of an appropriate material to form the strand will improve the biocompatibility and hemocompatibility of the stent 21, these qualities may be enhanced further by the application or bonding of an appropriate coating directly to the exterior surface of the stent 21. A sintered beaded structure may be applied also to the surface of the stent 21 to produce an interconnecting network of pores. By sinter-coating the surface, a biocompatible coating may also be mechanically bonded to the stent 21.

Stent 21 may be deployed in an integral tubular configuration. To aid deployment through naturally narrow or constricted blood vessels or other hollow organs, and because of the flexibility which the non-woven structure of the stent 21 provides, stent 21 may be compressed circumferentially. Because of the preferable use of materials which form bonding points 34 that are frangible, the compression of the stent 21 often will cause the bonding points 34 to fracture to a certain degree that may be required for each particular intended end use. Frangibility of the materials from which the bonding points are formed improves the flexibility of the stent 21 without sacrificing the structural integrity of the non-woven strand network. In its low profile state, stent 21 may be fitted within a catheter. The exterior diameter of the catheter must be smaller than the smaller dimension of the blood vessel or other hollow organ to be encountered by the catheter from its insertion to movement to the location at which the procedure is to be performed.

When used, the catheter is inserted percutaneously at an accessible location. The stent 21 may be released from the catheter at the appropriate intravascular site by advancing the stent 21 out of the catheter—such as by pushing a rod, inserted in the core of the catheter, against the stent 21—thereby also causing the stent 21, upon its advancement out of the catheter, to expand circumferentially. Utilizing frangible materials to form the bonding points facilitates the expansion of stent 21 without excessively decreasing its structural integrity. Allowed to remain at the location of the vascular defect, stent 21 is suitable for supporting the blood vessel or other body organ from its interior.

Alternatively, as illustrated in FIG. 2, the stent 21 may be deployed by fitting the stent 21 to the end of a catheter 41 and over a balloon 42 thereof. The expansion of the balloon within the blood vessel or other body opening 43 increases the circumference of the stent 21. If desired this expansion can have a differential characteristic which can be imparted to a stent 21 according to the present invention. When employed, this differential expansion feature allows the stent 21 to more readily conform to non-isodiametric vessel passageways and the like. Where the bonding points 34 are made from a frangible material, the stent 21 may be expanded without affecting the structural quality of the strand. Because of the mechanical durability of the stent 21, the stent 21 remains in place once it has been expanded. For example, it substantially as expanded by the balloon after the balloon has been deflated and the balloon catheter removed from the patient.

In the expanded configuration of the stent 21, the helix forming each layer 31, 32 of the stent 21 is reoriented, as shown in FIG. 3. The helix angle (with respect to the axis of the stent 21) increases as the stent 21 is radially expanded. The exterior diameter of the stent 21, as expanded, will be larger than the interior diameter of the blood vessel or other body opening in its pre-dilated, narrowed state, but slightly larger than, equal to or smaller than the diameter of the blood vessel or other body opening in its post-dilated state. The exact diameter of the stent 21 will be dictated by the amount to which the diameter of the stent 21 will expand to achieve the desired dilation and the degree, if any, to which the body opening wall is allowed to recoil.

A longitudinal slit 51 may be formed, such as by cutting, in order to form a stent 21a which has free longitudinal edge portions 52, 53 as illustrated in FIG. 4. As above, collapsing, fraying or unraveling of the strand material that terminates at the edge portions 52, 53 may be prevented by cropping the strand material closely to the bonding points 34 near the edge of the longitudinal slit 51, or by bending under or curling the strand ends.

A stent 21a with a longitudinal slit 51 may be deployed according to a variety of techniques. As above, the stent 21a may be compress-ed circumferentially so that the edge portions 52, 53 of stent 21a overlap each other in a manner generally shown in FIG. 4 and FIG. 5. In this compressed state, stent 21a may be fitted within a catheter and deployed generally as discussed hereinabove in connection with other embodiments of the invention. Alternatively, the stent 21a may be deployed by fitting the stent 21a to the end of a catheter and over a balloon, the latter of which is capable of expanding within and dilating the walls of a restricted body opening area. By expanding the balloon, the degree of overlap of the edge portions 52, 53 of the stent 21a is lessened and the circumference of the stent 21a increases. After the proper degree of expansion is achieved, the pressure within the balloon is decreased to deflate the balloon. The deflated balloon and catheter may be withdrawn allowing the expanded stent 21a, as shown in FIG. 6, to remain in place.

While these stents are particularly useful in vascular applications, they may also be suitable for use with about any hollow viscus or organ of the body. Examples include the tracheobronchial tree, the gastrointestinal system including the biliary tract, the genitourinary system including Fallopian tubes, ureters and urethra, the neurological system including the spinal canal and aquaduct, and the like.

It will be understood that the embodiments of the present invention which have been described are illustrative of some of the applications of the principles of the present invention. Numerous modifications may be made by those skilled in the art without departing from the true spirit and scope of the invention.

I claim:

1. A non-woven, generally tubular endoprosthesis for supporting living tissue, comprising:
   (a) a wound, non-woven generally tubular stiff strand network;
   (b) said stiff strand network includes a plurality of generally tubular layers of wire, one said layer overlying another said layer forming a generally tubular helically shaped member, said tubular member having an axial length and terminating at opposite ends;
   (c) a contact interface between said generally tubular layers, said contact interface including a plurality of locations at which a strand portion of said one layer intersects and contacts a strand portion of said another layer, said contact interface being points for bonding;
   (d) means for bonding said one layer to said other layer at said contact interface in order to form a non-woven, generally tubular endoprosthesis having attachment sites at said bonding points; and
   (e) said tubular layers of wire at the ends being cropped closely to said bonding points; and wherein the endoprosthesis has a diameter that is variable between a compressed percutaneous transluminally transportable diameter and an expanded, implanted diameter, said expanded diameter being for supporting an inside surface of a living tissue.

2. The endoprosthesis according to claim 1, wherein said bonding means includes means for thermally bonding said layers together at said attachment sites.

3. The endoprosthesis according to claim 1, wherein said bonding means includes means for adhesive bonding said layers together at said attachment sites.

4. The endoprosthesis according to claim 1, wherein said bonding means includes means for sintering said layers together at said attachment sites.

5. The endoprosthesis according to claim 1, further including a biocompatible and hemocompatible coating bonded to a surface of said endoprosthesis.

6. The endoprosthesis according to claim 1, further including a porous coating of biocompatible and hemocompatible sintered beads on said stiff strand.

7. The endoprosthesis according to claim 7, further including a carbon layer coating over said sintered beads.

8. The endoprosthesis according to claim 1, further including a porous coating of sintered beads to which a biocompatible coating is further bonded.

9. The endoprosthesis according to claim 1, wherein said layers have edge portions which terminate substantially at said attachment sites.

10. The endoprosthesis according to claim 1, wherein said means for bonding includes material that is frangible.

11. The endoprosthesis according to claim 1, wherein said stiff strand is formed from a metal or metal alloy.

12. The endoprosthesis according to claim 12, wherein said strand is formed from a metal selected from the group consisting of tantalum, titanium, steel, and alloys including same.

* * * * *

UNITED STATES PATENT AND TRADEMARK OFFICE
CERTIFICATE OF CORRECTION

PATENT NO. : 5,015,253
DATED : May 14, 1991
INVENTOR(S) : David C. MacGregor

It is certified that error appears in the above-identified patent and that said Letters Patent is hereby corrected as shown below:

Column 7, line 1 "compress-ed" should read --compressed--.

Signed and Sealed this

Twenty-ninth Day of September, 1992

Attest:

DOUGLAS B. COMER

Attesting Officer    Acting Commissioner of Patents and Trademarks